United States Patent [19]

Lowke et al.

[11] Patent Number: 4,467,032

[45] Date of Patent: Aug. 21, 1984

[54] IDENTIFICATION AND ENUMERATION OF MICROBIAL CELLS

[75] Inventors: George E. Lowke, Hurst, Tex.; Robert J. Meltzer, Long Valley, N.J.

[73] Assignee: Warner-Lambert Company, Morris Plains, N.J.

[21] Appl. No.: 371,906

[22] Filed: Apr. 26, 1982

[51] Int. Cl.³ .................... C12Q 1/04; C12Q 1/29; C12Q 1/06; C12M 1/34
[52] U.S. Cl. ........................ 435/34; 435/29; 435/32; 435/39; 435/291
[58] Field of Search ............ 435/29, 32, 34, 39, 435/291

[56] References Cited

U.S. PATENT DOCUMENTS 4,101,383  7/1978  Wyatt et al. .................. 435/32 X

OTHER PUBLICATIONS

Morris et al., The Effect of Neomycin and Streptomycin on the Electrical Polarisability of Aqueous Suspensions of *Escherichia cd.*, Biochimica et Biophysica Acta, vol. 392, 1975, (pp. 328–334).
Morris et al., The Effect of Antibiotics on the Electrical Polarisability of Aqueous Suspensions of Bacteria, Biochimica et Biophysica Acta, vol. 497, 1977, (pp. 253–259).

Primary Examiner—David M. Naff
Attorney, Agent, or Firm—Daniel A. Scola; Gary M. Nath

[57] ABSTRACT

A process and apparatus is disclosed for rapid and accurate identifying and enumerating of microorganisms. A sample believed to contain a certain microorganism is combined with an inhibiting reagent having a known specificity for the microorganism. The combined sample and inhibiting reagent is placed in an alternating current electrical field having a frequency sufficiently high to cause alignment of microbial cells in the sample. A polarized beam of laser light is then passed through the sample and the extent of birefringence is measured. The measured birefringence is compared with that of a control sample known to contain the microorganism under investigation to determine the microorganism in the sample.

13 Claims, 1 Drawing Figure

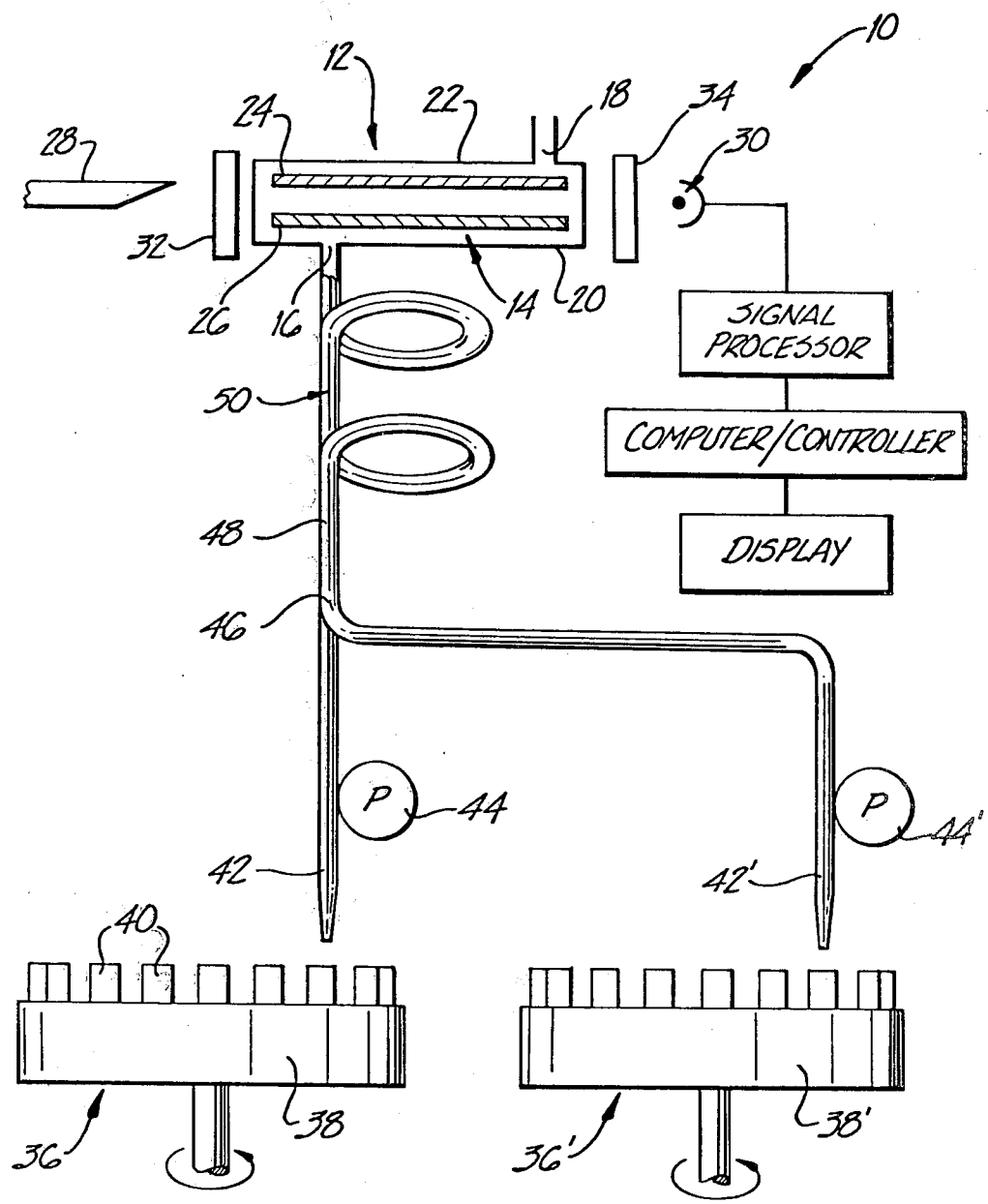

IDENTIFICATION AND ENUMERATION OF MICROBIAL CELLS

BACKGROUND OF THE INVENTION

1. Field of the Invention

The present invention relates to the identification of bacteria and more particularly to a method and apparatus for identifying bacteria utilizing electro-optical investigation.

2. Description of the Prior Art

Numerous methods have been developed and are presently utilized to identify various bacteria for purposes ranging from disease detection and treatment, to microbial research. Classically, samples of material believed to contain a given bacterium are investigated by first developing a culture on an appropriate growth medium, after which the presence or absence of the bacterium in question may be determined by a variety of further tests. In the instance of disease detection, this procedure can be extremely time-consuming, and may prove crucial in lifethreatening situations.

Certain basic investigations have been conducted recently in the area of electro-optics, in an effort to learn more about the structure and function of materials by their behavior in polarized light. In particular, several studies by V. J. Morris et als., noted that the application of an electrical field to a suspension of essentially non-spherical bacteria, resulted in a partial orientation of the bacteria, believed due to the development of a strong, induced dipole moment on the bacteria by the electric field. Carrying this further, V. J. Morris et als., Biochimica et Biophysica Acta, 392:328–334 (1975), investigated the effect of certain antibiotics on the electrical polarizability of aqueous suspensions of $E.$ $coli,$ and found that substantial changes in polarizability, measured as a function of light-scattering effect, took place. The authors theorized that the antibiotic molecules, in this study neomycin and streptomycin, were absorbed onto the bacterial surface, and resultingly reduced the surface charge of the bacteria and its apparent induced dipole moment. Further studies by V. J. Morris et als. relating to this subject comprise V. J. Morris et als., Microbios, 17:133–139 (1976), and Biochimica et Biophysica Acta, 497:253–259 (1977).

In general, it is known that when living cells are disposed in a liquid and the liquid is placed in an external electrical field, the cells will align themselves in the field. This alignment takes place because the cells have an asymmetric distribution of electrical charge on their surfaces. The asymmetric distribution of electrical charge on the surface of the cells may be a fixed property of the cell, in which case the cell is referred to as permanent dipole, or may be induced on the surface of the cell by the presence of the external electrical field, in which latter instance such charge distribution is referred to as an induced dipole. This asymmetry was identified and further investigated by Morris et al., by use of light-scattering optical techniques that measured by birefringence of the bacterial cells, i.e. the separation of a beam of light into two unequally refracted, plane polarized light beams. Thus far, however, this phenomenon has exhibited utility as an investigative avenue only, for the purpose of determining the electrical consequences of surface interactions between various particles, including living cells.

The present invention therefore attempts to unite the described phenomenon with appropriate methodology to address the need for a rapid and accurate assay technique for the detection and enumeration of particular microbial cells.

SUMMARY OF THE INVENTION

In accordance with the present invention, a method for detecting and enumerating microbial cells is disclosed which eliminates the time-consuming development of growth cultures. The method in its simplest aspect, comprises isolating a specified quantity of a fluid sample believed to contain a given microbial cell, combining a portion of the fluid sample with an inhibiting reagent having a known effect on the electrical polarizability of the microbial cell, placing the resulting fluid sample in an alternating current electrical field to cause the alignment of any microbial cells present, passing a polarized beam of laser light through the sample to measure the extent of birefringence, and comparing the measured birefringence with a reference measurement made with a control containing the cell under investigation without the inhibiting reagent.

A series of inhibiting reagents may be utilized to perform a series of sample preparations and measurements within a relatively short period of time, for example, on the order of ten to forty minutes, to provide a full identifying profile of the cell under investigation, so that conclusive and exact determinations can be made. The inhibiting reagents utilized in the present method may preferably be those materials that are not utilized clinically as antibiotics, as the microbial cells under investigation may develop resistance to these latter materials over time that would introduce inaccuracies in the identifying profile for the given microbial cell.

In a further aspect, the present method may include a pretreatment of the fluid or sample prior to the addition of the inhibiting reagent, to remove sample debris and other organisms not under investigation.

The present method may be performed in a sequential, automated manner in accordance with a further embodiment of the present invention.

Thus, an automated apparatus is also disclosed herein that comprises an electrical cell having at least two walls in parallel spaced apart relation, with paired electrodes located adjacent each of the walls. The electrodes are connected to an appropriate voltage source and may establish an induced electrical field between them, through which the microbial samples may be passed. An optical sensing assembly comprising a laser light source and a detector, are positioned so that a beam of laser light passes through the electrical cell, between the electrodes, and contacts the detector upon its emergence from the cell. An automated microbial sample delivery means, including, for example, parallel conduits and pumps, may mix and deliver microbial samples in sequence, to the flowthrough cell for examination.

The laser light detector is connected to an electrical signal processing means to translate the observed birefringence into an electrical signal capable of comparison with reference measurements taken with a control sample containing the particular microbe under investigation. A time delay loop may be interposed between the sample conduits and the electrical cell, in the instance where reaction between reagents is desired, such as between an antibody and an antigen.

The ability to conduct such investigation and to perform the present method in this automated manner, facilitates the rapid and accurate determination of the presence of a given microbial cell. The present method lends itself to a variety of applications, including immunoassays, coagulation measurements and possibly the detection of cancerous cells.

Accordingly, it is a principal object of the present invention to provide a method for the rapid and accurate detection and enumeration of microbial cells.

It is a further object of the present invention to provide a method as aforesaid that eliminates the need for development of growth cultures of samples prior to investigation.

It is a still further object of the present invention to provide a method as aforesaid, which may be performed in an automated manner.

It is a still further object of the present invention to provide an apparatus for the electro-optical detection and identification of microbial samples.

It is a still further object of the present invention to provide an apparatus as aforesaid that facilitates automated delivery, examination and analysis of microbial samples, on a sequential basis.

Other objects and advantages will become apparent to those skilled in the art from a review of the ensuing description which proceeds with reference to the following illustrative drawing.

BRIEF DESCRIPTION OF THE DRAWING

The FIGURE is a schematic representation of a possible apparatus useful in accordance with the method of the present invention.

DETAILED DESCRIPTION

The present invention relates to a method for detecting and enumerating microbial cells in a rapid and accurate manner, that is susceptible to automated performance. The method utilizes electro-optical examination to identify microbial cells on the basis of their individual birefringent characteristics.

As stated earlier, studies by V. J. Morris et als., enumerated previously and presently incorporated herein by reference, demonstrated that the application of an electrical field to a quantity of cells in liquid suspension, causes the cells to orient or align themselves in the field, because the cells have an assymetric distribution of electrical charge on their surfaces. This assymetrical distribution causes the cell to behave like a dipole, and in most instances this dipolar behavior is induced, rather than permanent. Accordingly, when the electrical field is withdrawn, the bacterial cells recover and move out of their assumed alignment.

The phenomenon described above, i.e. the alignment of the bacterial cells in the induced electrical field, and the relaxation of those cells after the field is withdrawn, can each be measured, and such measurements may be made in the practice of the present method. Specifically, the amount of birefringence that occurs when a light source is directed through the sample containing the inductively charged microbial cells, provides information leading to the identification of the presence of the cells under investigation. The measurement of the period of relaxation, i.e. the time that elapses after the withdrawal of the electrical field, during which the microbial cells return to a non-aligned conformation, provides information as to the size of the microbial cells under investigation. Both parameters may be investigated and determined rapidly and sequentially by the present method.

The present method broadly comprises isolating a sample of a material suspected to contain a particular microbial cell. The material may comprise a body fluid, such as urine, in the instance where bacteriuria is suspected and confirmatory testing is necessary.

While the quantity of sample material necessary for testing may vary, a feature of the present invention is that minute amounts of material may be utilized, and placed into liquid suspensions, with portions of the liquid suspensions as small as one milliliter or less in volume capable of investigation and disclosure of the microbial cells in question. A modest quantity of sample material may therefore provide an abundance of individual sample portions for a series of sequential investigations, in the instance where it may be desirable to develop an identifying profile of the cell under investigation. This latter technique is utilized in the present method and will be discussed later on herein.

Prior to the processing of a given sample, it may be necessary to preliminarily process the sample, for example, to reduce the retained charge of the sample material, or to eliminate electrical interference that may result from the presence of extraneous matter in the sample material. Samples may therefore be appropriately screened, and if found in need of such treatment or processing, may be subjected to filtration from a suspension, centrifugation and the like, to remove sample debris, and other treatments appropriate to reduce the charge of the sample, so that accurate readings may be taken when the sample is placed in the electrical field and the light beam is passed therethrough.

After the sample has been readied as described above, a quantity of one or more inhibiting reagents may be added. Inhibiting reagents are generally defined as those materials that form some surface interaction with the microbial cells under investigation, and that may result in a modification of the charge density of the cell walls. It should be borne in mind that the present method seeks to identify microbial cells by the characteristics of the cell walls alone, rather than by the internal anatomy or physiology of the cell. Thus, the outer or surface charge of the cell wall will vary as the cell wall is placed in contact with differing reagents, and this alteration can be quantified and utilized for purposes of identification.

In one aspect, a single sample portion may be prepared and investigated, in which case a quantity of an individual inhibiting reagent would be added thereto. The present invention also contemplates that a profile of a particular microbe may be developed by the preparation of a series of control samples, each in combination with a different inhibiting reagent, so that a profile of birefringence readings would be available that would clearly define the specific microbe under review. Thus, a series of sample portions may be prepared, as described above, and thereafter a quantity of different inhibiting reagents may be individually added to respective sample portions, so that the profile of birefringence data developed for the samples under investigation could be compared with a profile developed for control samples, to provide an accurate identification in the event that the microbe under investigation is present in the sample.

As brought out in the articles by Morris et als., discussed earlier herein, certain antibiotics were found to serve in such inhibitory capacities in combination with bacteria, so that changes in the intensity of birefringence were evident. In the present method, however, the materials utilized as inhibiting reagents should preferably not include those antibiotics or other compounds that are utilized clinically in conjunction with the microbes under investigation, as the possibility exists that the microbes may develop resistance to these materials that would alter and possibly invalidate the control profile utilized for final identification through comparison.

Keeping this caveat in mind, the panel of materials that may be utilized may include materials such as plant lectins, appropriate non-toxic inert dyes, various vitamin and/or drugs, such materials selected in each instance for their known inhibitory effect upon the microbial cells under investigation. The exact quantity of each inhibiting reagent may be different, however, should be an amount thereof sufficient to cause an inhibition or reduction in the surface charge of the microbial cells. This can be verified by preliminary preparations of control samples with particular inhibiting agents, and the development of a satisfactory profile for use. Naturally, the selection of particular inhibiting reagents and amounts of such reagents added to respective samples may vary in accordance with the present invention, and those materials and amounts specified herein are provided by way of illustration and not by way of limitation.

After the addition of the inhibiting reagent to the sample portion is complete, the resulting sample is placed in an electrical field by the imposition of an alternating current, with a field strength sufficient to align any of the cells under investigation. Generally, the electrical field may be imposed by a pair of parallel, spaced apart electrodes, between which the sample will be placed or will pass.

Thus, the sample may be placed on an appropriate slide or in an ampoule, that may be manually disposed between the electrodes, or a flow-through chamber may be utilized with electrodes disposed therein, in the instance where automated delivery and investigation of sample portions is desired. In this connection, reference is made to the FIGURE which schematically and through block diagram representation, illustrates a possible apparatus for automated sample preparation and examination.

Referring to the FIGURE, an automated apparatus 10 for the practice of the present method is shown. Apparatus 10 comprises an electrical cell 12 comprising a chamber 14 having an inlet and an outlet 18. Chamber 14 includes paired walls 20 and 22 that are located generally parallel to each other and in spaced apart relation, to contain a quantity of the microbial sample under investigation.

Paired electrodes 24 and 26 are located adjacent respective walls 20 and 22 and are likewise spaced apart from each other. Electrodes 24 and 26 are adapted to receive electrical current from a voltage source, not shown, and establish an induced electrical field between them, that is thus applied to the sample material located in cell 12. In this way, the microbial cells under investigation in the sample, are caused to move into electrical alignment with the imposed field, as a function of their polarizability.

The electrical field applied between electrodes 24 and 26 may vary in intensity, and is preferably an alternating current field of a frequency sufficiently high to achieve discernible cell orientation. For example, a pulse of high frequency current, on the order of 50 Hz or greater has been utilized to achieve sufficient cellular orientation for purposes of examination and identification. Applied current may reach as high as 700 Hz or greater within the scope of the present invention, and the reliance upon specific maxima or minima in this regard is not contemplated herein.

Referring again to the FIGURE, apparatus 10 includes an optical sensing assembly comprising a laser light source 28 shown schematically, that is positioned to pass a beam of laser light through cell 12 and between electrodes 24 and 26. A laser light detector 30 is positioned in alignment with light source 28 as illustrated, to receive the light emerging from cell 12. In addition, a polarizer 32 is provided between light source 28 and cell 12, so that the laser light emitted is polarized, as required, during its passage through the sample. Also, an analyzer 34 is disposed between the cell 12 and detector 30, for the purpose of blocking input light, and thereby to limit the light received by detector 30 to that emitted by light source 28.

Apparatus 10 may be automated as indicated, and employ an automated sample delivery means in fluid registry with cell 12, to sequentially convey microbial samples to inlet 16. In particular, sample delivery means may comprise at least one sample reservoir 36 for the purpose of containing the microbial samples prior to their examination. In the present illustration, plural sample reservoirs 36 and 36' are shown, that comprise carousel conveyors 38 and 38', each conveyor carrying a plurality of respective dispensers 40 and 40'. In the illustration in the FIGURE, carousel 38 may carry dispensers 40 containing the microbial samples, while carousel 38' carries dispensers 40' having comparable inhibitor reagents. By means described hereinafter, samples may be sequentially mixed with corresponding reagents prior to introduction into cell 12, so that reactions between cells and inhibitors can take place just prior to electro-optical examination.

The delivery means also includes at least one secondary conduit and preferably a plurality of secondary conduits 42 and 42', that are adapted to extend from respective reservoirs 36 and 36', to inlet 16. Conduits 42 and 42' may, in one embodiment, be adapted for sequential reciprocation into fluid registry with dispensers 40 and 40', so that specific reagents and samples may be withdrawn and mixed as described herein.

The sample delivery means includes one or more fluid pumps 44 and 44' that reside in corresponding fluid registry with secondary conduits 42 and 42' for the purpose of transferring the respective fluid contained within the reservoirs, to the conduits and thereafter to chamber 14.

In the instance where an apparatus of the type illustrated in the FIGURE is prepared, plural conduits 42 and 42' are brought to a merger point or fluid junction 46 that is located between reservoirs 38 and 38' and inlet 16. In the instance, for example, where samples and their respective inhibiting reagents are disposed in individual carousels 36 and 36', conduits 42 and 42' convey the individual fluids to fluid junction 46, at which point the conduits merge and the respective fluids are mixed. The mixed fluids then travel through a primary conduit 48, and proceed to inlet 16.

In the instance, for example, where it is desired to delay the delivery of the sample to the electrical cell 12, an appropriate time delay means 50 such as the delay loops illustrated, may be disposed along primary conduit 48, intermediate its path to inlet 16. This is of value, in the instance where the sample under investigation comprises a mixture of an antigen and an antibody, as time delay means 50 permits the reaction of the antigen and antibody to take place and to go to completion prior to the entry into cell 12.

The time delay means may be the series of loops schematically represented in the FIGURE, or may comprise a holding station, not shown, where the sample fluid is retained prior to transporting it to cell 12. The exact construction of this element may vary, and the present invention is not limited to a particular structure or manner of operation.

Referring again to the FIGURE, apparatus 10 also includes an electrical signal processing means connected with the laser light detector 30 that translates variations in birefringence caused by each microbial sample, into an electrical signal of quantitative data for analysis and comparison with the results of control tests. As indicated by the block representation, the signal from the detector may be passed through an appropriate signal processor, and, for example, may be converted to an appropriate digital signal. This signal may then be fed into a computer having, for example, comparator circuits that would recognize and correlate the incoming signal with stored signals representing the results of the control tests. This comparison could then be immediately identified by a digital display, and, as discussed hereinafter, the entire investigation and measurement of a given sample may take place within milliseconds. Naturally, the extent of measurement, the nature of the specific investigation, and the number of samples under test will cause corresponding variation in testing time.

Generally, while the apparatus described above will include the primary elements identified and explained, certain variations in the construction and operation of these elements will be possible within the scope of the present invention. Thus, the present disclosure is not intended to be limited to the exact construction disclosed above, but is to be considered illustrative of an apparatus broadly embracing the structural elements described, and capable of modification, including the substitution of equivalent structures, within the scope of the invention.

OPERATION

Referring again to the FIGURE, samples may be disposed in the individual dispensers 40 and 40' as discussed earlier, in the instance where inhibiting reagents are placed in separate containers for mixture thereafter. Secondary conduits 42 and 42' may dip down or otherwise make fluid contact with dispensers 40 and 40', respectively, at which time pumps 44 and 44' may commence operation to draw up the respective fluids. Pumps 44 and 44' may operate like step motors, so that predetermined quantities of fluid are transported in defined increments and so that individual samples will arrive for investigation with minimal contamination by adjacent sample preparations.

The respective samples travel through secondary conduits 42 and 42' and, as described earlier, are mixed at fluid junction 46. After mixture, for example, in the instance of a microbial sample and its corresponding inhibiting reagent, the resulting mixed fluid travels through primary conduit 48, and may, in instances appropriate, travel through time delay means 50.

The mixed sample thereafter passes through primary conduit 48 and is delivered to electrical cell 12 through inlet 16. Upon the completion of delivery of the sample to cell 12, the voltage source, not shown, is activated and an electrical field is established between electrodes 24 and 26. As mentioned earlier, the electrical field may vary depending upon the nature of the sample under examination, and is generally set at a frequency sufficiently high to achieve discernible cell orientation. The electrical field may be maintained for a period of time sufficient to achieve cellular alignment. The length of time that the electrical field is maintained may vary, depending upon the size and electrical characteristics of the cells involved, and the invention is not limited to a specific time range. For example, in the instance where antibody/antigen reactions are being investigated, the time period must be extended to permit the investigation to proceed as a rate method, to observe the change in birefringence that takes place as the antibody and the antigen react to form the complex.

Similarly, in the instance where cellular size is to be identified, the electrical field may be withdrawn, while continuing to observe the extent of birefringence, so as to determine the time period during which relaxation or recovery of the cellular elements from alignment with the field takes place and is completed. This measurement can be taken in sequence, following the identification of the microbial cells, by the simple withdrawal or shutdown of the electrical field, as stated.

The identification of the microbial cells occurs when the laser light source 28 is directed through the sample disposed between electrodes 24 and 26. As indicated earlier, effective birefringence may be measured in an instance, for example, when the sample portion is as small as one milliliter or less in volume, and the laser light beam is one millimeter in width and one hundred millimeters in travel.

The actual measurement of birefringence of specific samples, is predicated upon the observation that, if a sample containing bacteria or other microbial cells is subjected to a pulse of high frequency current, the bacteria or cells will orientate within that field. If the pulse is of sufficient length, it has been determined that an orientation equilibrium will be achieved, and a finite degree of orientational order will be obtained. In the instance where dilute suspensions are subjected to a sufficiently high frequency electrical field, for example having a rms amplitude E, the resultant equilibrium change in scattered intensity is seen to vary to some extent with the square of the amplitude. Thus, small changes in amplitude of the applied current will elicit discernible changes in the scattering intensity, that can be measured and used as a means for cellular identification.

As described earlier, the laser beam emitted by light source 28 passes through cell 12 and thereafter through analyzer 34 to detector 30. The signal received by detector 30 is processed and may be compared with data from a control sample, and a display of this correlation can be instantaneously visually available.

As noted earlier, the actual time required to prepare and investigate a given microbial sample may be as little as ten minutes, including the preparation of the sample for application of the electrical field and the laser beam. The measurement of birefringence alone, may occur within milliseconds from the application of the light source 28. As mentioned earlier, the preparation and testing of a plurality of samples, and the development of a profile for comparison to a control profile involves a greater time expenditure, and may take as long as forty minutes. Nonetheless, this represents a substantial reduction in time for the accurate identification of microbial cells, and constitutes one of the significant advantages of the present invention.

The present invention also contemplates the measurement of the size of the microbial cells, as well as their identification. In this connection, and as described earlier, size of particles or cells may be determined by the measurement of the amount of time that it takes for the cells to move out of alignment with the direction of the electrical field, after the field is withdrawn. This measurement may take place independently, in the instance where the field is applied, the cells are aligned, and then the field is withdrawn. At this point, a time measurement may take place and the light source may be passed through the suspension, to observe the changes in birefringence that reflect the movement of the cells out of alignment with the field.

Both identification and particle size may be measured sequentially and efficiently, by first measuring the birefringence of the suspension under the application of the electrical field, and thereafter withdrawing the electrical field, and measuring the elapsed time for recovery or movement of the cells out of alignment therewith. The comprehensive and efficient nature of this combined investigation is clear.

In the practice of the present method, further factors should be considered and controlled, to assure uniformity of results. In particular, the temperature of all materials should remain constant through their examination, as temperature is known to have a modifying effect on birefringence results. Likewise, the pH of the suspensions under test should be regulated as much as possible, to conform to the known pH of the microbial samples under test, as variations in acidity or alkalinity could effect the charge of the suspensions and result in inaccurate readings. Naturally, other factors, such as avidity and titer must be controlled, as well, to assure accuracy and uniformity in testing.

As mentioned earlier, the present method is applicable to a variety of investigations, in addition to the identification of microbial cells. For example, the reaction between antigens and antibodies may be studied in this manner, by measuring the change in birefringence, as the antigen or antibody react to form the complex. In this instance, time delay means 50 may be of use, as it would permit the respective solutions containing the antigen and the antibody and combine and commence their interaction and incubation. The application of the electrical field is thus conducted and the parameters of time and light intensity are measured, to identify the reaction of the antibody and the antigen, as well as making measurements of the same.

In similar fashion, the coagulation process may be studied, to determine the change in size of the protein molecules, as molecular charge distribution most probably changes during this process. Accordingly, several measurements could be taken at intervals during this process, to measure the fine structure of the coagulation. This technique could also be applied to blood platelet function as the determination of birefringence may be made in milliseconds and may thus be able to capture any pathologies of platelet function that would occur very early in aggregation.

A still further possible application of the present method, is in the detection of cancer. This stems from the knowledge that the cell surface charge on T-cells changes for malignant populations. Thus, the detection of malignancy could be made more easily by the present method, than by electrophoresis, which is present in use.

The operation of the electrical field during the present method may take several approaches, inasmuch as an alternating current field is set up, and changes in amplitude of the current are known to elicit changes in birefringence that will identify certain cells. In particular, these considerations are pertinent to instances where the method is to be utilized as a rate method, over time, such as in the measurement of antibody/antigen interaction. In the instance where the flow-through arrangement of the FIGURE is utilized, and a time delay 23 such as the loop illustrated in the FIGURE permits incubation, a differential amplifier may be utilized to subtract the signal received from the uncombined components, from that of the complex. In this connection, the signal received from the presence of the uncombined materials may be converted into digital form and then subtracted from a similarly digitized signal received for the complex, having determined in this computation the time interval reflecting the delay from incubation.

Alternate techniques may be utilized to observe this distinction, such as "chirping" the drive voltage, i.e. sweeping the frequency with the control to the electrical field, to identify maxima in the modulation and thereby to possibly separate molecular species. Also, the voltage pulse passing through electrical cell 12 may be driven at a rate such that the signal for the uncombined materials can barely keep up. In such instance, a phase lock amplifier may be utilized, and by observing the quadrature signal, minute amounts of the complex could be detected within larger amounts of the uncombined materials.

The foregoing details of operation would relate primarily to the instance where the method is to be utilized to measure time as well as light-scattering. These techniques are simply exemplary of considerations that may be taken into account in the practice of the present method, and are not intended to confer limitation on the present invention.

It is to be understood that the invention is not limited to the illustrations described and shown herein, which are deemd to be merely illustrative of the best modes of carrying out the invention, and which are suitable of modification of form, size, arrangement of parts and details of operation. The invention rather is intended to encompass all such modifications which are within the spirit and scope and defined by the claims.

What is claimed is:

1. A method for identifying and enumerating microbial cells in a sample of unknown material comprising:
   A. isolating a quantity of said sample of unknown material;
   B. combining said sample with at least one inhibiting reagent having a known specificity for said microbial cells;
   C. placing said combined sample in an alternating current electrical field, said electrical field having a frequency sufficiently high to cause any of said microbial cells present in said sample, to move into alignment therewith;
   D. passing a polarized beam of laser light through said combined sample and measuring the extent of birefringence thereof; and
   E. comparing the birefringence of said combined sample with the birefringence of a control sample, known to contain the microbial cell under investigation, in combination with said inhibiting reagent;

F. wherein said control sample is prepared and measured in accordance with Steps A–D herein, and the presence of said microbial cell in the unknown sample is determined from said comparison.

2. The method of claim 1 wherein said sample material is disposed in a non-toxic, electrically inert liquid, prior to participation in Step B.

3. The method of claims 1 or 2 wherein said sample material is eliminated of extraneous matter to reduce the retained charge and eliminate electrical interference.

4. The method of claim 3 wherein said sample material is treated by centrifugation.

5. The method of claim 3 wherein said sample material is treated by filtration.

6. The method of claim 1 wherein said inhibiting reagents comprise materials not in clinical use, that exert an effect on the cell wall of said microbial cells.

7. The method of claim 6 wherein said inhibiting reagents are selected from the group consisting of antimicrobial compounds; plant lectins; non-toxic, inert dyes; vitamin compounds; and mixtures thereof.

8. The method of claims 1, 6 or 7 wherein a plurality of said samples are prepared, and each sample is combined with a different inhibiting reagent.

9. The method of claim 1 wherein said electrical field has a frequency of at least 60 Hz.

10. The method of claim 1 wherein said electrical field ranges in frequency from about 60 Hz to about 700 Hz.

11. The method of claim 1 wherein during Step D said electrical field is withdrawn, and said laser beam is maintained for a period of time sufficient to permit said cells to move out of alignment with said electrical field.

12. The method of claim 1 wherein said beam is one millimeter in width, and has a line of travel of 100 millimeters.

13. The method of claim 1 wherein the Steps thereof are performed in a continuous, atomated manner.

* * * * *